United States Patent [19]

Schultz et al.

[11] 4,148,831

[45] Apr. 10, 1979

[54] METHOD OF PREPARING 1,1-DIFLUOROETHYLENE

[75] Inventors: Neithardt Schultz; Peter Martens, both of Rheinfelden; Hans-Joachim Vahlensieck, Wehr, all of Fed. Rep. of Germany

[73] Assignee: Dynamit Nobel Aktiengesellschaft, Cologne, Fed. Rep. of Germany

[21] Appl. No.: 800,605

[22] Filed: May 25, 1977

[30] Foreign Application Priority Data

Jun. 5, 1976 [DE] Fed. Rep. of Germany ....... 2625470

[51] Int. Cl.$^2$ ................................................ B01J 1/10
[52] U.S. Cl. ............................. 260/653.5; 204/163 R
[58] Field of Search ................. 204/163 R; 260/653.5

[56] References Cited

U.S. PATENT DOCUMENTS

| 2,644,845 | 7/1953 | McBee | 204/163 R |
| 4,053,529 | 10/1977 | Martens | 260/653.5 |

FOREIGN PATENT DOCUMENTS 360831  8/1973  U.S.S.R. ................................ 260/653.5

Primary Examiner—Leland A. Sebastian
Attorney, Agent, or Firm—Sprung, Felfe, Horn, Lynch & Kramer

[57] ABSTRACT

Method of preparing 1,1-difluoroethylene from 1,1-difluoroethane by photochlorinating 1,1-difluoroethane to 1,1-difluoro-1-chloroethane and immediately thereafter reacting the reaction products of the photochlorination at temperatures between 550 and 750° C. without isolation of the 1,1-difluoro-1-chloroethane.

7 Claims, No Drawings

METHOD OF PREPARING 1,1-DIFLUOROETHYLENE

BACKGROUND OF THE INVENTION

1. Field Of The Invention

This invention relates to the preparation of 1,1-difluoroethylene. More particularly this invention relates to a process for the preparation of 1,1-difluoroethylene by photochlorination of 1,1-difluoroethane with chlorine and pyrolysis of the reaction products thereof without isolation of chlorination by-products or the like.

2. Discussion Of The Prior Art

It is known to prepare 1,1-difluorethylene directly from 1,1-difluorethane. The difluorethane is reacted with chlorine at temperatures between 600 and 650° C. Chlorosubstituted difluorethylenes are also formed as by-products (cf. U.S. Pat. No. 2,722,558). In this process the high temperature is extremely disadvantageous, since it causes the known metallic reactor materials to be attacked by the chlorine. For the production of 1,1-difluorethylene on a large technical scale, therefore, this process is unsuitable.

Furthermore, the 50 to 60% yields of 1,1-difluorethylene obtained in this method are entirely unsatisfactory. An increase in yield can be achieved by performing the reaction in the presence of dichlorodifluoromethane. However, even then the yields are still unsatisfactory (U.S. Pat. No. 2,723,296). This variant of the process, however, does not solve the problem of preventing the corrosion of the reactor material, so that this process does not eliminate the disadvantages of the process mentioned above.

To eliminate the disadvantages of these two known processes, a twostep process is described in German Offenlegungsschrift No. 21 45 975, in which 1,1-difluorethane is chlorinated in parallelly conducted process steps, and independently thereof, 1,1-difluor-1-chlorethane is pyrolytically cleaved to 1,1-difluorethylene. In this process it is expressly pointed out that the pyrolysis is to be performed with a pure 1,1-difluor-1-chlorethane from which the hydrogen chloride formed in the chlorination has been removed, as well as any excess chlorine that may be present.

This process has the disadvantage that two complete process steps are performed and only the working up (recovery) of the process products is performed in common. For the separation of the process products, however, a relatively great investment in apparatus is required. In addition, the yields of 1,1-difluoroethylene, which must be related only to the pyrolytic reaction, amount to less than 90%, which is unsatisfactory for operations on a large commercial scale.

The problem thus existed of preparing 1,1-difluorethylene from 1,1-difluorethane so as to obtain yields of more than 95%, with correspondingly high transformations. The process is furthermore to be performed in a single step, and requires only a small investment in apparatus. In addition, the problem existed of finding a process in the performance of which little or no corrosion is caused by chlorine to the reactor material.

It is an object of this invention, therefore, to provide a process for the preparation of 1,1-difluoroethylene from 1,1-difluoroethane whereby yields of 1,1-difluoroethylene in excess of 95% are realized.

It is a further object of this invention, therefore, to provide a simple process for the preparation of 1,1-difluoroethylene from 1,1-difluoroethane wherein large investments in apparatus are not required.

It is a further object of this invention to provide such a process whereby the manipulative procedures can be carried out continuously without the separation of intermediates.

These and other objects of this invention will become more apparent from the following description and claims.

SUMMARY OF THE INVENTION

Broadly, this invention contemplates a process for the preparation of 1,1-difluoroethylene which comprises subjecting 1,1-difluoroethane to photochlorination in the presence of chlorine and thereafter subjecting the photochlorination products thereof to pyrolysis without isolation of any 1,1-difluoro-1-chloroethane.

It has been found, in accordance with this invention, that exceptional high yields of 1,1-difluoroethylene can be realized by a simple two-step process which does not require the isolation of purification of any of the products resulting from the first step. In accordance with the process, in a first step, 1,1-difluoroethane is chlorinated with chlorine. The photochlorination products are thereafter directly sent to a pyrolysis step. The photochlorination products consist mainly of 1,1-difluoro-1-chloroethane which in the pyrolysis (second) step is converted to 1,1-difluoroethylene.

The photochlorination of the 1,1-difluoroethane is accomplished by subjecting the 1,1-difluoroethane to chlorine and directing light rays thereon. Generally speaking, the photochlorination is carried out in a glass or other transparent reactor and wavelengths of light are directed thereto. These wavelengths of light can be in the visible or in the ultraviolet range. The preferred light wavelength range is between 500 and 600 nm.

The molar ratio of difluoroethane to chlorine during the chlorination should be about 1:1. A slight excess of chlorine can be tolerated. If possible, the said molar ratio must not be greater than 1:1.2.

The chlorination is performed at temperatures between 0° and 150° C. The preferred temperature range is between 20° and 70° C. The time of stay in the chlorination reactor, which consists preferably of glass, are to be insofar as possible between 20 and 100 seconds, with respect to 0° C. and the empty reactor.

The photochlorination products are then sent directly to the pyrolysis step. They are neither isolated nor treated by any means before entering in the pyrolysing reactor.

The chlorination products are then directly subjected to the dehydrochlorination by pyrolysis. They consist mainly of 1,1-difluoro-1-chloroethane and hydrogen chloride, plus small amounts of more highly chlorinated fluorochloroethanes. The content of these chlorinated by-products is generally less than 1%.

The dehydrochlorination is performed at temperatures between 500° and 750° C. The reaction products forming in the chlorination of the 1,1-difluoroethane, mainly the hydrogen chloride that is liberated, bring it about that the pyrolysis leads to the desired 1,1-difluorethylene with a virtually 100% yield. These high yields are obtained especially when the dehydrochlorination reactor is packed with material having a good thermal conductivity. Suitable material of this kind is, for example, metal chips which are not attacked under the conditions of the reaction, such as, for example, nickel chips. The preferred pyrolysis temperature is between 600° and 720° C.

The time of stay in the pyrolysis reactor is to be between 1 and 150 seconds, with reference to the empty reactor and 0° C. The preferred range is between 2.5 and 90 seconds.

The reactor must be made of a material which is not attacked under the conditions of the reaction. Particularly suitable are tubular reactors of nickel.

In general, the dehydrochlorination is performed at atmospheric pressure or at the pressure which establishes itself in the course of the reaction. This pressure is generally not greater than about 1.1 atmospheres. Basically, however, it is also possible to operate at higher pressures say up to 5 atmospheres.

The process of the invention is preferably performed continuously. In this case the chlorination reactor and the dehydrochlorination reactor are connected directly together. The reaction products, after leaving the second reactor, are washed with water or dilute alkali hydroxide solution, and then dried. The gas mixture obtained contains as impurities mainly unreacted difluorethane, which can easily be separated in a known manner from the 1,1-difluorethylene.

EXAMPLES

EXAMPLE 1

A gaseous mixture composed of 1,1-difluorethane (DFE) and chlorine in a molar ratio of 1:1.1 is passed through a glass reactor having a useful capacity of 3.6 liters, under irradiation from a 250-Watt halogen metal vapor lamp. The temperature in the glass reactor is held between 30° and 40° C. The gas flow amounts to 6.3 moles per hour (3.0 moles/h DFE; 3.3 moles/h Cl$_2$), so that a time of stay of 92 seconds, with respect to 0° C. and the empty reactor, results.

The reaction mixture obtained is fed, after emerging from the glass reactor, directly into a second reactor (cleavage reactor) of pure nickel. This tubular cleavage reactor, which has an inside diameter of 36 mm and a heated length of 600 mm, packed filled with nickel chips for better heat distribution. The reaction temperature is maintained by external heating at 680° to 700° C. From the data given above, it follows that, for the empty reactor, the time of stay is 15.5 seconds, with respect to 0° C.

The reaction mixture leaving the nickel reactor is washed with dilute caustic soda solution and then dried. A mixture of organic compounds is obtained, having the following composition determined by gas chromatography:

99.0% $CH_2 = CF_2$
0.5% $CH_3 - CHF_2$
0.5% higher-boiling compounds.

With respect to the sum of the two reactions, a yield is thus achieved of 99.5%, and a transformation of 99.5%.

It is possible by means of an additional line equipped with suitable shut-off means to feed the product leaving the glass chlorination reactor through a washing and drying apparatus and analyze it. It consists of:

99.1% $CH_3 - CF_2Cl$, and
0.9% higher-boiling compounds.

EXAMPLE 2

A gaseous mixture of 4.0 moles/h of DFE and 4.4 moles/h of Cl$_2$ is passed through the experimental arrangement described in Example 1. The reaction temperature in the glass reactor is maintained at 55° C., resulting in a time of stay of 69 seconds, with respect to 0° C. In the nickel reactor the reaction temperature is held at 680° at 700° C. as in Example 1. The time of stay accordingly amounts in this case to 11.5 seconds (0° C.) with respect to the empty reactor volume of 610 ml.

The gas mixture is transferred as in Example 1 from the chlorination reactor directly to the cleavage reactor. After leaving the cleavage reactor, the reaction product is washed and dried. It consists of:

98.9% $CH_2 = CF_2$
0.6% $CH_3 - CHF_2$
0.5% higher-boiling compounds.
Total transformation: 99.4%; total yield: 99.5%.

EXAMPLE 3

(Given for purposes of comparison)

To demonstrate the surprisingly good success of the arrangement set up in Examples 1 and 2, a comparative experiment was conducted in which a washing and drying apparatus was installed between the glass reactor (chlorination of DFE) and the nickel reactor (cleavage of DFCE) in order to free the chlorination reaction product of the hydrogen chloride and residual traces of chlorine. The reaction temperatures in the two reactors and the rest of the conduct of the experiment were the same as described in Example 2.

After the washing and drying of the product emerging from the nickel reactor, the following composition resulted:

59.8% $CH_2 = CF_2$
2.9% $CH_3 - CHF_2$
23.8% $CH_3 - CF_2Cl$
13.4% by-products, mostly ethylenes containing fluorine and chlorine.

The total transformation was 97.1%, and the total yield had dropped to 61.7%.

What is claimed is:

1. A process for preparing 1,1-difluoroethylene which comprises subjecting 1,1-difluoroethane at a temperature between 20° and 70° C. to photochlorination employing a molar ratio of 1,1-difluoroethane to chlorine of 1:1.0–1.2 to form 1,1-difluoro-1-chloroethane and feeding the reaction products thereof directly to a nickel pyrolysis reactor and pyrolyzing the reaction products without isolation of the 1,1-difluoro-1-chloroethane.

2. A process according to claim 1 wherein the pyrolysis is effected at temperatures between 550° and 750° C.

3. A process according to claim 1 wherein the pyrolysis is performed for a period of between 1 and 150 seconds.

4. A process according to claim 1 wherein the pyrolysis is performed in the presence of nickel chips.

5. A method of preparing 1,1-difluoroethylene which consists essentially of:

A. Photochlorinating 1,1-difluoroethane at a temperature in the range of 20° to 70° C. in the presence of chlorine employing a 1,1-difluoroethane to chlorine molar ratio of 1:1.0–1.2 by directing light rays on the reaction mixture which light rays are in the visible or ultraviolet range; and B. Pyrolyzing the reaction products thereof in a nickel reactor without isolation of any 1,1-difluoro- 1-chloroethane at a temperature between 550° and 750° C.

6. A process according to claim 5 wherein the process is conducted continuously by continuously feeding chlorine and 1,1-difluoroethane into a photochlorination reactor, maintaining the reactants therein for a period of time of between 20 and 100 seconds, with respect to 0° C. and an empty reactor, at a temperature between 0° and 150° C. and passing the reaction products directly to said pyrolysis reactor without separating any 1,1-difluoro-1-chloroethane and therein pyrolizing the photochlorination products at a temperature between 550° and 750° C. employing a residence time in the pyrolysis reactor of between 1 and 150 seconds.

7. A process according to claim 6 wherein the pyrolysis is performed at a temperature between 600° and 720° C.

* * * * *